United States Patent [19]
Erskine

[11] Patent Number: 5,685,855
[45] Date of Patent: Nov. 11, 1997

[54] PROTECTED NEEDLE CATHETER PLACEMENT DEVICE WITH SAMPLING PROVISIONS AND METHOD FOR ITS USE

[76] Inventor: Timothy J. Erskine, 1160 Stone Valley Way, Sandy, Utah 84094

[21] Appl. No.: 685,293

[22] Filed: Jul. 23, 1996

[51] Int. Cl.⁶ .................................................. A61M 5/00
[52] U.S. Cl. ........................ 604/168; 604/110; 604/198
[58] Field of Search ............................. 604/168, 256, 604/900, 110, 198, 162

[56] References Cited

U.S. PATENT DOCUMENTS

| | | | |
|---|---|---|---|
| 4,747,831 | 5/1988 | Kulli | 604/110 |
| 4,917,671 | 4/1990 | Chang | 604/168 |
| 5,209,739 | 5/1993 | Talalay | 604/195 |
| 5,575,777 | 11/1996 | Cover et al. | 604/198 |

*Primary Examiner*—Sam Rimell
*Assistant Examiner*—Luke J. Yeh
*Attorney, Agent, or Firm*—Arthur D. Dawson

[57] ABSTRACT

A needle assembly has an elongate hollow handle with a proximal end with provisions for attaching a fluid handling device and a distal end with an opening. The assembly has a needle with a distal point, a proximal end and an open passageway. The assembly also has an elongate substantially transparent needle hub with a distal end portion that has the needle fixedly attached. The needle hub is disposed for coaxial slidable movement within the hollow handle from a first position wherein the needle projects outwardly from the handle. The needle hub includes an elongate flashback chamber inside that is fluidly connected to the needle for viewing flashback. The needle hub is operatively biased for axial movement from the first position to a proximal rest position within the handle. When the needle hub is in the proximal position, the needle is substantially contained within the handle. The hollow handle has a latch that releasably retains the needle hub in the first position and an operative trigger to release the latch so that the operatively biased hub moves axially. The assembly has a hollow flexible tube inside the hollow handle extending from the proximal end of the hub to the attachment for the fluid handling device. When the hub is in the first position, the tube connects the flashback chamber to the attachment for the fluid handling device. When the latch is released and the needle hub moves to the proximal rest position, the flexible tube substantially collapses.

14 Claims, 6 Drawing Sheets

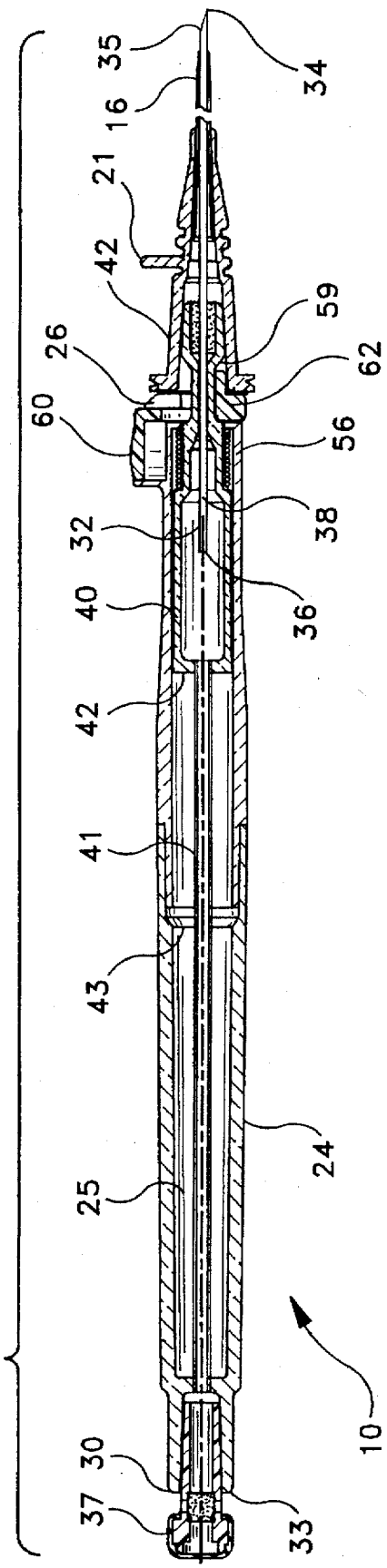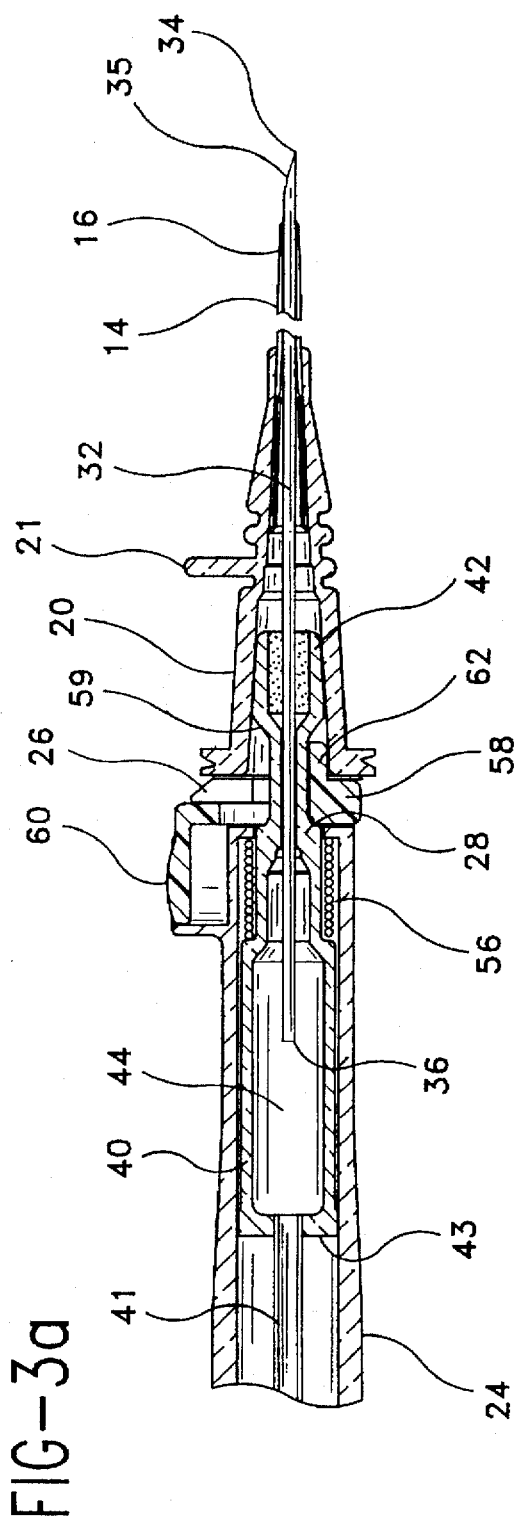

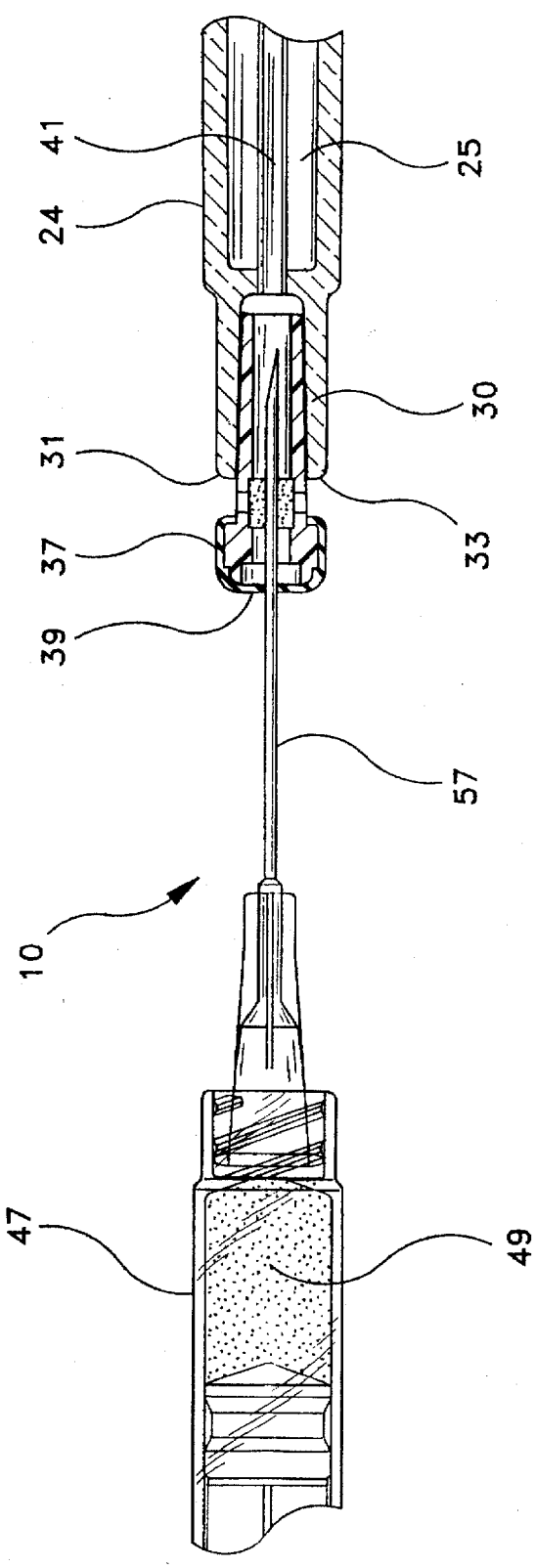

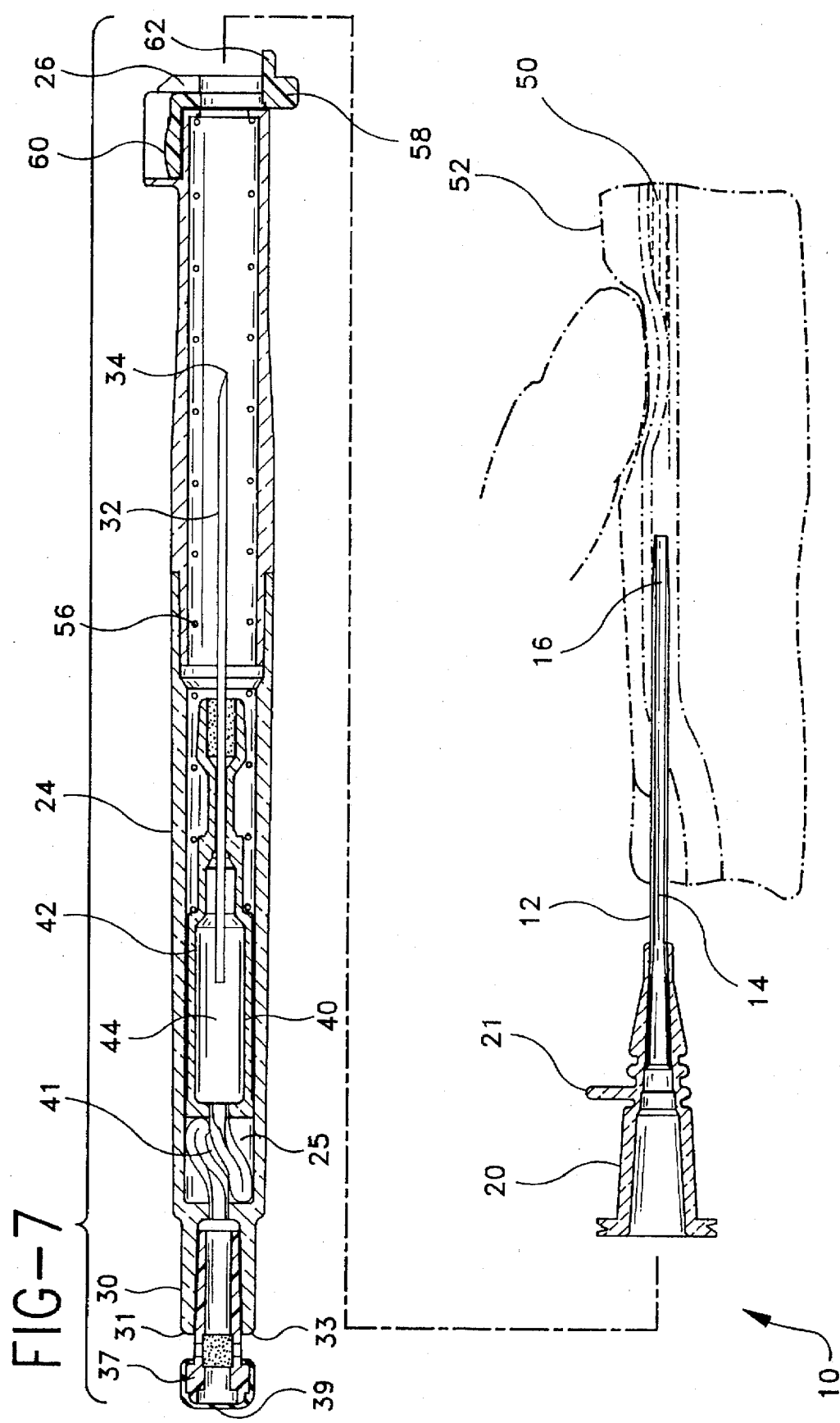

PROTECTED NEEDLE CATHETER PLACEMENT DEVICE WITH SAMPLING PROVISIONS AND METHOD FOR ITS USE

FIELD OF INVENTION

This invention is generally related to intravascular catheters and devices for placing an intravascular catheter and more particularly to a catheter placement device with a protected needle retraction system having fluid sampling provisions.

BACKGROUND

An intravascular catheter is generally a flexible small diameter tube inserted into a patient's blood vessel to allow withdrawal or addition of fluid. Typically, a practitioner places the catheter by locating a target blood vessel for the placement, then pierces the patient's skin and the blood vessel wall with an inserter needle, uses the needle to lead the catheter into the vessel and then removes the needle, leaving the catheter in the vessel. Catheters may be inserted into blood vessels either through the bore of the needle or over-the-needle. In this disclosure, catheters that are inserted over-the-needle are described. Additionally, a convention is followed in this disclosure using the term "proximal" to refer to the portion of the device closest to the practitioner and the term "distal" for the portion of the device toward the patient or away from the practitioner.

Over-the-needle catheters are generally supplied already mounted on an inserter needle in a sterile, ready-to-use, unit package. In its simplest form, the over-the-needle catheter generally resembles one tube slidably fit within another tube, the flexible catheter being outermost with a sharp beveled point inserter needle slidably fit within the catheter bore so that the sharp distal inserter needle point projects beyond a gently tapered distal end of the catheter. In placement of these over-the-needle catheters, the needle, with the catheter outside, is held by the practitioner, generally with the point bevel face up, longitudinally aligned with the target blood vessel. The needle is then inserted at a shallow angle through the patient's skin into the blood vessel. The practitioner then often determines that the needle is properly positioned within the blood vessel by allowing a small quantity of the patient's blood to flow through the hollow needle, impelled by the patient's blood pressure, so that the small quantity of blood can be seen at the rear of the needle. This practice of using the patient's blood to signal proper placement of needle within the target vessel is termed "flashing or flashback." The flashing step has the purpose of confirming that the catheter is properly inserted into the blood vessel. Once the proper placement is confirmed, the practitioner applies finger pressure to the vessel over the distal tip of the needle and the catheter to occlude further blood flow, withdraws the needle and attaches a fluid handling device to the catheter hub. Catheters are placed both in veins and in arteries. When an artery is the target blood vessel, the practitioner needs to confirm that the flash is arterial blood, not venous blood. Often, a blood sample is analyzed to confirm that the catheter needle is placed in an artery, not a vein. To obtain a blood sample, several manipulative steps may be required. Alternatively, a practitioner may choose to allow a sufficient amount of the patient's blood to escape to confirm that the pulsatile blood flow characteristic of arterial blood is present.

During these manipulative steps, small amounts of the patient's blood may be released. Additionally, once the inserter needle is removed, it is a "blood-contaminated sharp" and must be properly handled. With the recognition by the medical device art of the risk of transmission of Acquired Immunosuppressive Deficiency Syndrome (AIDS) by blood contaminated sharps, devices such as disclosed in U.S. Pat. No. 4,747,831 were developed. The patent discloses a cannula insertion set with safety retracting needle. The device disclosed in the patent provides a cannula insertion needle projecting from a hollow handle into which the needle is withdrawn after the placement is completed. Anyone handling the device subsequent to the withdrawal is thus substantially protected from the contaminated needle because it is contained within the inserter handle. There is no disclosure in this patent regarding sampling blood during the catheter placement.

An improvement to retractable-needle cannula insertion devices is disclosed in U.S. application Ser. No. 08/422,662. The disclosure of the improvement includes provisions for containing and controlling the flashing by providing a chamber connected to the needle to allow visualization of the blood and substantially retain the blood within the device when the needle is removed and the device is in the disposal process. This patent also does not disclose any provision for sampling the blood flashback or withdrawal of blood from the flashback chamber.

These disclosed devices have provided practitioners with improvements in the placing of catheters and handling of catheter inserter needles as well as control and visualization of blood flashback. However, there is still a need for a catheter needle inserter assembly that enables a practitioner to take a blood sample from the flashback chamber or empty the flashback chamber without removing the needle from the catheter. Such a device is disclosed below.

SUMMARY

A preferred needle assembly of the present invention includes an elongate hollow handle with a proximal end defining an opening, and a distal end. The assembly has an elongate needle with a sharp distal point, a proximal end and an open passageway therethrough. The assembly also has an elongate needle hub with a distal end portion having the proximal end of the needle fixedly attached therein and a proximal end. The needle hub is sized and disposed for coaxial slidable movement within the hollow handle. There is an elongate flashback chamber for viewing blood flashback within the needle hub that is fluidly connected to the proximal end of the needle. The assembly also has a hollow flexible tube within the hollow handle extending from the proximal end of the hub to the proximal end of the hollow handle to fluidly connect the flashback chamber to the opening in the proximal end of the hollow handle when the hub is in a first position with the needle projecting distally from the handle. The tube is substantially collapsed when the hub is in a proximal position where the needle is substantially contained within the handle.

The needle assembly of the invention allows a practitioner to confirm a placement of a catheter in a target blood vessel, not only by observing the blood flashback in the flashback chamber, but also allows positive confirmation that the placement is in an artery by enabling a blood sample to be withdrawn before the inserter needle is removed from the catheter. Alternatively, the practitioner may empty the flashback chamber and allow it to refill to confirm pulsatile blood flow characteristic of arterial blood. The ability to confirm placement before withdrawal of the needle from the catheter improves the efficiency of placement of catheters, since if the placement is not in the desired vessel, the practitioner can partially withdraw the assembly with the catheter still attached to repeat the penetration into the target. Arterial catheter placement is important in anesthesia practice, blood gas measurement and other critical care applications.

BRIEF DESCRIPTION OF THE DRAWINGS

FIG. 3 is a cross-sectional view of the invention of FIG. 1 taken along the line 3—3;

FIG. 3a is an enlarged view of a portion of the view of FIG. 3;

FIG. 6 is an enlarged partial cross-sectional view, analogous to FIG. 3, of the proximal portion of the invention of FIG. 1 as placed in a patient's blood vessel with a fluid handling device attached; and FIG. 7 is a cross-sectional view of the invention of FIG. 1, after release of the needle withdrawal mechanism.

DETAILED DESCRIPTION

Figure 1:
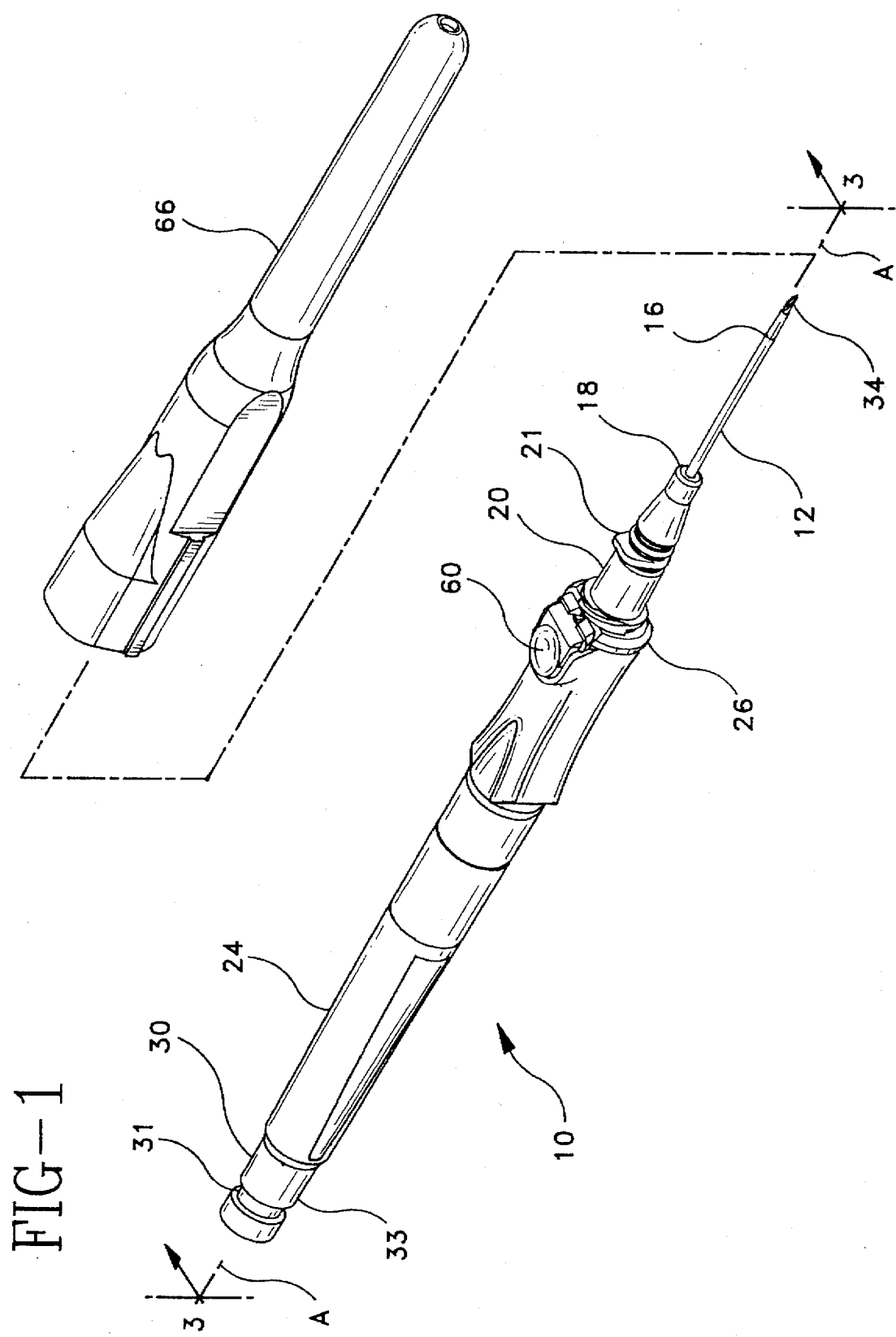
FIG. 1 is a partially exploded perspective view of the preferred catheter placement device of the present invention.
Figure 2:
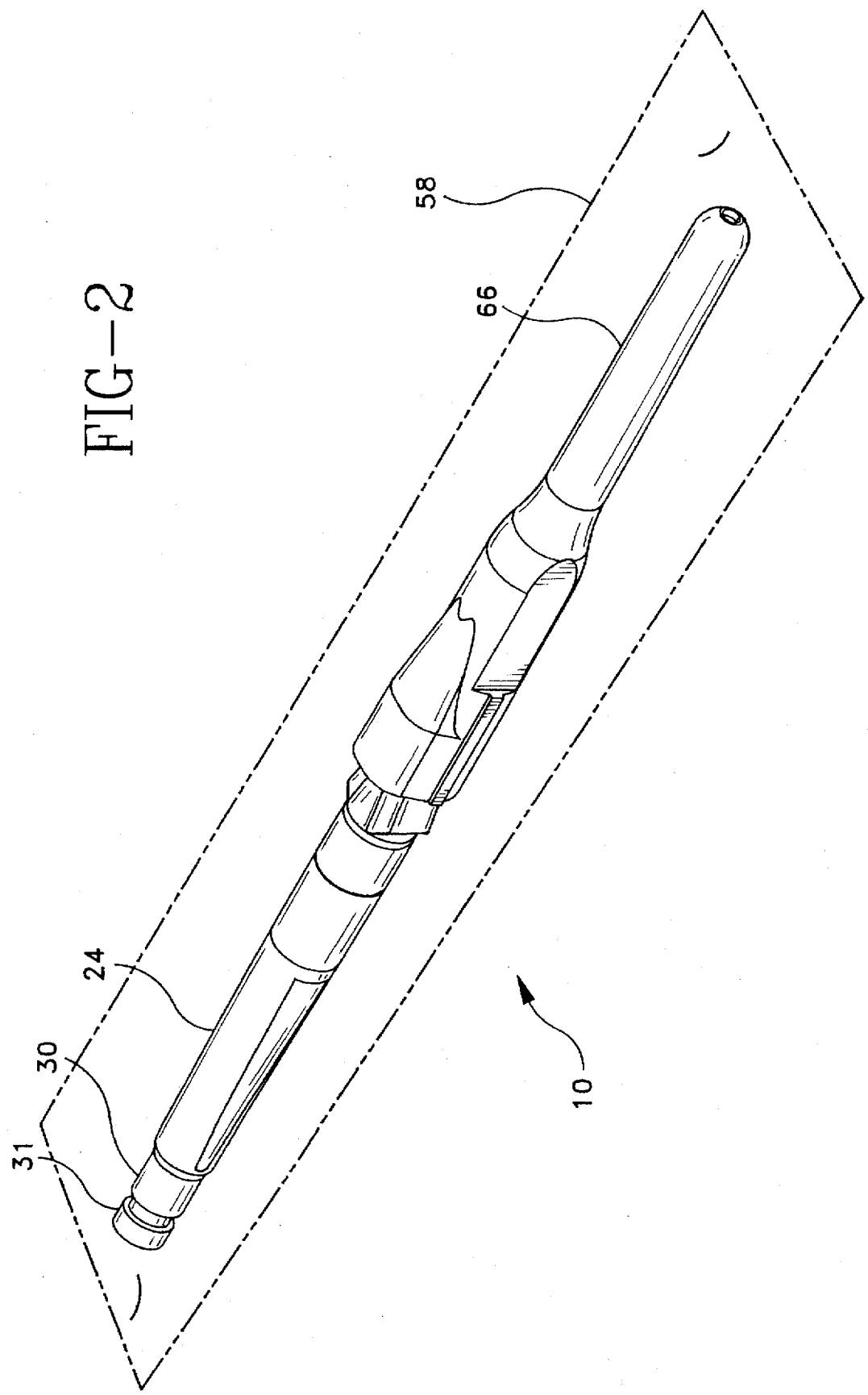
FIG. 2 illustrates the invention of FIG. 1 assembled and placed in a package.

While this invention is satisfied by embodiments in many different forms, there is shown in the drawings and is herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1–7, a preferred needle assembly 10 of the present invention with a longitudinal axis A includes an elongate catheter 12 with an open bore 14 therethrough, a tapered distal end 16 and a proximal end 18 with a hub 20. Assembly 10 has an elongate hollow handle 24 that has a cavity 25 therewithin. Hollow handle 24 has a distal end 26 that has an opening 28 therethrough into cavity 25 and a proximal end 30 with a fitting 31, preferably a female luer fitting 33, for attaching a fluid handling device to handle 24. Assembly 10 also has an elongate needle 32 that has a sharp distal point 34, preferably having a beveled surface 35, a proximal end 36 and an open passageway 38 therethrough. Preferred assembly 10 has a substantially transparent elongate needle hub 40 with a distal end portion 42 with needle proximal end 36 fixedly attached therein. Needle 32 is coaxially slidably disposed within catheter bore 14 so that sharp distal point 34 of the needle projects beyond the tapered distal end of catheter 12 and catheter hub 20 is releasably mounted onto distal end portion 42 of the needle hub. Needle hub 40 is slidably disposed for coaxial movement within the cavity in hollow handle 24 from a first position, best seen in FIGS. 3 and 3a, where distal end portion 42 of the needle hub projects axially outwardly from the hollow handle through opening 28.

Figure 4:
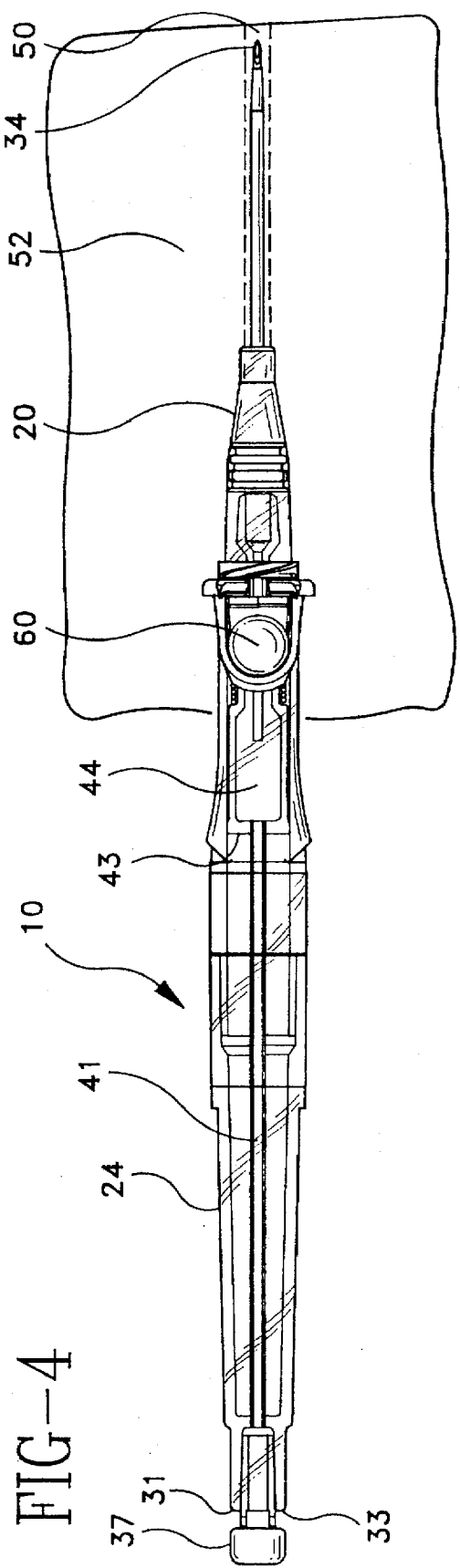
FIG. 4 is a top plan view of the invention of FIG. 1 with the shield removed, aligned for placement into a patient.
Figure 5:
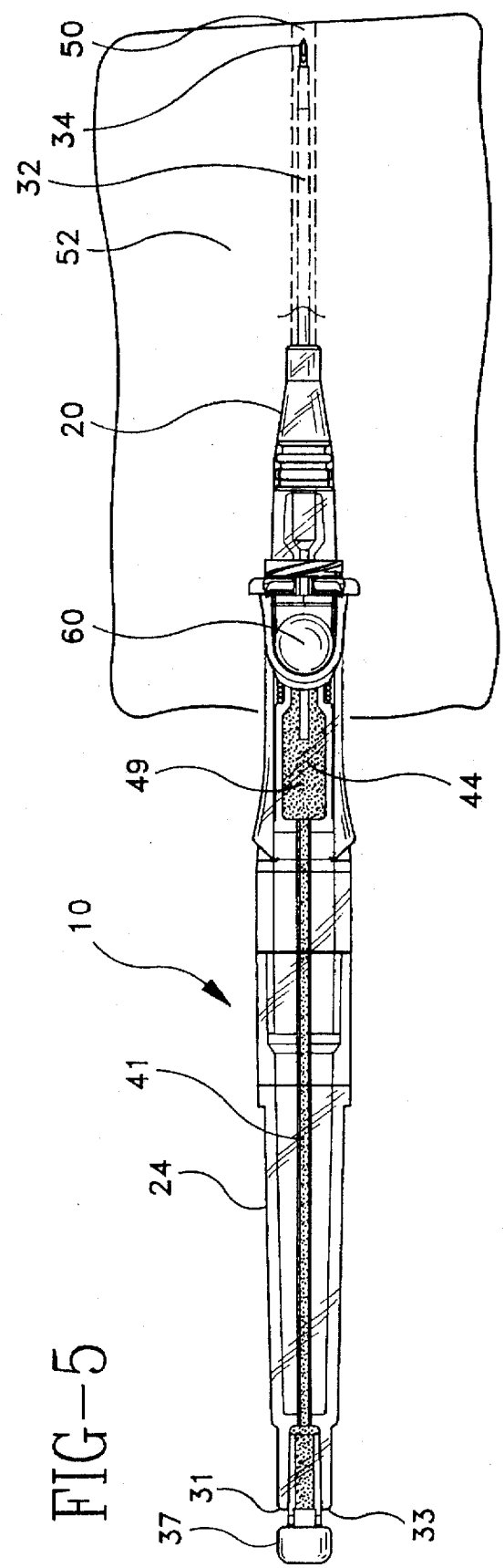
FIG. 5 is a top plan view of the invention of FIG. 1 illustrating placement of the device into a patient's blood vessel.

Referring to FIGS. 3 and 3a, needle hub 40 has an elongate flashback chamber 44 that is fluidly connected to open passageway 38 at proximal end 36 of needle 32. Assembly 10 has a thin flexible hollow tubing 41 fluidly connecting a proximal end 43 of needle hub 40 to fitting 31 at proximal end 30 of hollow handle 24. When needle hub 40 is in the first position, needle 32 projects distally outside and is axial to hollow handle 24. Prior to use, when needle hub 40 is in the first position with catheter 12 mounted on the distal end portion of needle hub 40 that preferably extends into catheter hub 20, hollow tubing 41 allows a fluid handling device to transfer fluid into or from flashback chamber 44. Referring to FIGS. 4 and 5, when the assembly of the invention is used for placing a catheter in a patient's blood vessel 50, the practitioner longitudinally aligns assembly 10 with vessel 50 above the patient's skin 52 and then penetrates the patient's skin so that the needle point penetrates the vessel 50 at a shallow angle. When the target vessel is penetrated, blood 49 "flashes" into needle 32 and into flashback chamber 44 providing an immediate visual indication, as seen in FIG. 5, to the practitioner that the needle point has entered a blood vessel. When the target vessel is a vein, this flashback indication is generally sufficient for the practitioner to proceed to occlude the vein with finger pressure as shown in FIG. 7, and to withdraw the needle from the catheter into the hollow handle. In cases where the target vessel is an artery, it is often desirable to confirm the arterial placement by either allowing a larger volume of blood to pass into the needle to confirm that the blood delivery is "pulsatile" or to withdraw a sample for blood gas analysis. The assembly of the invention preferably has a vented plug 37 fitted into female luer fitting 33 to allow air to be displaced from the flashback chamber 44. Additionally, plug 37 may be fitted with a pierceable septum 39 to facilitate transfer of fluid from or to chamber 44. Catheter assembly placement device 10 of the invention allows the practitioner to place a fluid handling device, a syringe or the like, on proximal fitting 31 and utilize tubing 41 empty flashback chamber 44 or to withdraw a sample using a syringe 47 with a piercing element, such as a needle 57, for analysis, best seen in FIG. 6, before removing needle 32 from the patient's blood vessel. The fluid handling device may also be attached by removing plug 37 and mounting the fluid handling device directly on proximal fitting 31.

Needle hub 40 is operatively biased, preferably by a coil spring 56, for coaxial movement from the first position, as shown in FIGS. 3, 3a, 4 and 5 to a proximal position, best seen in FIG. 7, where needle 32 with the sharp distal point 34 is withdrawn into cavity 25 to be substantially within hollow handle 24 and tubing 41 is substantially collapsed.

Hollow handle 24 includes a releasable latch 58, with a trigger 60 for releasing latch 58, that engages needle hub 40 to retain needle hub 40 in the first position and, disengages, when actuated by the practitioner, to release needle hub 40 for movement to the proximal position within hollow handle 24. Trigger 60 is preferably located at or a proximal distance from distal end 26 of the hollow handle 24.

Suitable materials for forming hollow handle 24, catheter hub 20 and needle hub 40 include, but are not limited to, thermoplastic polymeric resins such as polycarbonate, polystyrene, polypropylene and the like. Handle 24 is preferably formed from a transparent material. Needle 32 and coil spring 41 are preferably formed from a stainless steel alloy or the like. Since tubing 41 must readily substantially collapse when needle hub 40 is withdrawn to the proximal rest position the tubing is preferably formed from a resilient, low durometer material. Suitable materials for forming tubing 41 include, but are not limited to, silastic rubber, polyurethane, polyvinylchloride and the like. Tubing 41 preferably has an internal diameter between about 0.25 mm to about 1.6 mm with a wall thickness between about 0.07 mm to about 0.8 mm. Tubing 41 is fixedly attached between proximal fitting 31 and distal end 43 of needle hub 40.

Suitable attachment methods include, but are not limited to solvent bonding, adhesive bonding, heat bonding, mechanical wedging, barbed fittings and the like.

Referring again to FIGS. 1 and 2, assembly 10 is preferably supplied with a shield 66, sized and shaped to fit onto hollow handle 24 to obstruct inadvertent access to needle 32 and trigger 60 for releasing latch 58. Preferably, assembly 10 with shield 66 is placed within a sealed package 68, as indicated in phantom in FIG. 2, that is formed from materials substantially resistant to the passage of microorganisms. The sealed package is then preferably exposed to conditions sufficient to render any microorganisms within the package substantially non-viable. Suitable package materials include, but are not limited to, paper, plastic film, non-woven materials, combinations thereof and the like. Suitable conditions for rendering microorganisms non-viable include, but are not limited to, chemical sterilants such as ethylene oxide, hydrogen peroxide vapor and the like; and exposure to ionizing radiation such as gamma radiation, beta particles and the like. The packaged assembly is then considered to be sterile until the package is opened. When materials are selected for forming assembly 10 and package 68, there should be consideration of the particular materials' compatibility with the planned sterilization conditions.

A preferred method for a practitioner to place a catheter into a patient's target blood vessel 50 using assembly 10 of the present invention is illustrated in FIGS. 4–7. The method includes opening package 68, removing the shielded assembly 10 then dismounting shield 56 and exposing catheter 12 with projecting needle point 34. The method includes positioning assembly 10 substantially longitudinally aligned with target blood vessel 50 with bevel 35 facing substantially away from a surface 53 of the skin, as shown in FIG. 4, and inserting it at a shallow angle, preferably less than about 35 degrees, into surface 53 of the skin, so that distal point 34 enters target blood vessel 50, as shown in FIG. 5. The method then includes observing a blood flashback 49 in blood flashback chamber 44, as best seen in FIG. 5. As described above, the method also includes the practitioner attaching a fluid handling device to fitting 31 and emptying or withdrawing a sample from flashback chamber 44 when this step is required by the procedure.

After confirming placement of needle 32 in the target blood vessel, the method includes advancing catheter 12 distally axially along needle 32 into position in the blood vessel, preferably using upwardly extending tab 21. As placement of catheter 12 is achieved, the method includes the practitioner placing a finger from his other hand on the patient's skin over the blood vessel. By placing his finger on the patient's skin and applying sufficient pressure on the skin, the practitioner thereby occludes blood flow through the catheter, as shown in FIG. 7. The method then includes the practitioner withdrawing the needle from bore 14 of the catheter by depressing trigger 60 and releasing latch 58 so that spring 56 urges needle hub 42 into the proximal position within hollow handle 24. The practitioner may then attach any desired fluid handling device to catheter hub 20 and commence the planned treatment. Hollow handle 24 with needle 32 substantially within it may then be disposed of according to the facility's disposal protocol.

Preferably, when assembly 10 is manufactured, needle 32 is rotationally oriented in hub 40 so beveled surface 35 is substantially aligned with trigger 60 for releasing latch 58. Further, catheter hub 20 preferably includes an outwardly projecting tab 21 that is also substantially aligned with the beveled surface and the trigger when the catheter hub is mounted on the needle hub. The alignment of the needle point beveled surface, the catheter hub tab and the trigger provides for an intuitive and ergonomic usage of the assembly. When the assembly is unshielded in preparation for usage by the practitioner, the alignment of the needle bevel and trigger substantially directs the practitioner's grasp of the hollow handle to the proper position for insertion into the patient with needle point bevel surface 35 facing upward as shown in FIG. 3. Following placement, as shown in FIG. 5, the practitioner is able to confirm the proper placement in the patient's blood vessel by observation of the blood flashback in flashback chamber 44. The catheter hub is distal to trigger 60 and the hollow handle. The practitioner then occludes the blood vessel with a finger from his other hand, as shown in FIG. 7, uses outward projecting tab 21 to urge catheter 12 distally and dismount catheter hub 20 from needle hub 40. The practitioner is then able to actuate trigger 60 to release latch 58 so that needle hub 40 is moved to the proximal position.

Referring to FIGS. 3 and 3a, latch 58 preferably includes a projection 62 that is contained within catheter hub 20 when the catheter is fully mounted on needle hub 40 as shown in FIGS. 3 and 3a. Projection 62 substantially prevents inadvertent actuation of latch 58 while catheter hub 20 is mounted on needle hub 40 by substantially preventing movement of the latch. When catheter hub 20 is dismounted from needle hub 40 as catheter 12 is advanced into the patient's blood vessel, projection 62 is no longer contained within catheter hub 20 and the practitioner's actuation of trigger 60 is able to urge latch 58 from the position where it retains needle hub 40 in the distal position to a position where the needle hub is no longer retained. The bias provided by spring 56 then urges the needle hub to the proximal position.

The catheter placement assembly of the invention, by having the flashback chamber, allows the practitioner to recognize almost instantaneously when the needle point has penetrated the vessel wall and entered the patient's blood vessel. Then, since the flashback chamber is connected to the luer fitting at the proximal end of the hollow handle of the assembly, the practitioner then may easily confirm the placement in the target vessel by emptying the flashback chamber or by withdrawing a sample. Rapid visualization of flashback substantially reduces the potential for incidents of needle penetration through the far wall of the blood vessel by allowing the practitioner to stop advancing the needle as soon as it enters the blood vessel, and the sampling capability allows confirmation of proper placement.

What is claimed is:

1. A needle assembly comprising:
   an elongate hollow handle with a proximal end defining an opening, and a distal end;
   an elongate needle having a sharp distal point, a proximal end and an open passageway therethrough;
   an elongate needle hub with a distal end portion having said proximal end of said needle fixedly attached therein and a proximal end, said needle hub sized and disposed for coaxial slidable movement within said hollow handle, said needle hub including an elongate flashback chamber for viewing blood flashback therewithin, said flashback chamber fluidly connected to said proximal end of said needle; and
   a hollow flexible tube within said hollow handle extending from said proximal end of said hub to said proximal end of said hollow handle, said tube fluidly connecting said flashback chamber to said opening in said proximal end of said hollow handle when said hub is in a first position wherein said needle projects distally from said handle, said tube being substantially collapsed when said hub is in a second position wherein said needle is substantially contained within said handle.

2. The needle assembly of claim 1 wherein said opening in said proximal end of said hollow handle includes a female luer fitting fluidly connected to said hollow tube.

3. A needle assembly comprising:

an elongate hollow handle with a proximal end and a distal end having an opening therethrough, said proximal end including means for attaching a fluid handling device;

an elongate needle having a sharp distal point, a proximal end and an open passageway therethrough;

an elongate needle hub with a distal end portion having said proximal end of said needle fixedly attached therein, said needle hub sized and disposed for coaxial slidable movement within said hollow handle from a first position wherein said needle projects distally outwardly from said handle, said needle hub including an elongate flashback chamber for viewing blood flashback therewithin, said flashback chamber fluidly connected to said proximal end of said needle;

said needle hub being operatively biased for an axial movement from said first position to a proximal rest position within said handle wherein said needle with said sharp distal point is substantially contained within said handle, said hollow handle further including means for releasably retaining said needle hub in said first position and operative release means to release said hub for said axial movement to said proximal rest position; and a hollow flexible tube within said hollow handle extending from said proximal end of said hub to said means for attaching said fluid handling device on said hollow handle, said tube fluidly connecting said flashback chamber to said means for attaching said fluid handling device when said hub is in said first position so that a blood sample may be drawn from said flashback chamber, said tube being substantially collapsed when said hub is in said proximal rest position.

4. The needle assembly of claim 3 further including an elongate catheter having an open bore therethrough, a tapered distal end and a proximal end having a hub, said catheter coaxially slidably disposed over said needle with said catheter hub releasably mounted on said distal end portion of said needle hub and said sharp distal point of said needle projected beyond said tapered distal end of said catheter.

5. An over-the-needle catheter placement assembly comprising:

an elongate catheter having a open bore therethrough, a tapered distal end and a proximal end having a hub;

an elongate hollow handle with a proximal end and a distal end having an opening therethrough, said proximal end including means for attaching a fluid handling device;

an elongate needle having a sharp distal point, a proximal end and an open passageway therethrough;

an elongate needle hub with a distal end portion having said proximal end of said needle fixedly attached therein, said needle being coaxially slidably disposed within said catheter bore with said catheter hub mounted on said distal end portion of said needle hub and said sharp distal point of said needle projected beyond said tapered distal end of said catheter, said needle hub sized and disposed for coaxial slidable movement within said hollow handle from a first position wherein said needle and said distal end portion of said needle hub project distally outwardly from said handle, said needle hub including an elongate flashback chamber for receiving and viewing blood flashback therewithin, said flashback chamber fluidly connected to said proximal end of said needle;

said needle hub being operatively biased for an axial movement from said first position to a proximal rest position within said handle wherein said needle with said sharp distal point is substantially contained within said handle, said hollow handle further including means for releasably retaining said needle hub in said first position and operative release means to release said hub for said axial movement to said proximal rest position; and a hollow flexible tube within said hollow handle extending from said proximal end of said hub to said means for attaching said fluid handling device on said hollow handle, said tube fluidly connecting said flashback chamber to said means for attaching said fluid handling device when said hub is in said first position so that a blood sample may be drawn from said flashback chamber, said tube being substantially collapsed when said hub is in said proximal rest position.

6. The catheter placement assembly of claim 5 wherein said retention means comprises a ledge on said needle hub releasably engaged with a latch member located a proximal distance from said distal end of said hollow handle.

7. The catheter placement assembly of claim 6 wherein said release means comprises a trigger to release said latch from said ledge, said trigger located a proximal distance from said distal end of said hollow handle.

8. The catheter placement assembly of claim 5 wherein distal end of said hollow handle has an inside surface and said needle hub includes a shoulder, and wherein said assembly has a coil spring coaxially about said needle hub, said spring being compressed between said shoulder on said needle hub and said inside distal surface of said hollow handle when said needle hub is in said first position, said compressed coil spring thereby providing said operative bias for said movement of said hub to said proximal rest position.

9. The catheter placement assembly of claim 5 wherein said assembly further includes a removable shield covering said catheter and said needle.

10. The catheter placement assembly of claim 9 wherein said assembly is placed in a package formed from materials substantially resistant to the passage of microorganisms and exposed to conditions sufficient to render any microorganisms therein substantially nonviable.

11. The catheter placement assembly of claim 5 wherein said means for attaching a fluid handling device comprises a female luer fitting for mounting a fluid handling device.

12. The catheter placement assembly of claim 11 wherein said female luer fitting has a removable vented plug fitted therein, said plug allowing air to be displaced from said flashback chamber as blood flashback enters through said needle.

13. The catheter placement assembly of claim 12 wherein said removable vented plug further includes a pierceable septum so that a blood sample may be removed from said flashback chamber without removal of said plug.

14. An over-the-needle catheter placement assembly comprising:

an elongate catheter having a open bore therethrough, a tapered distal end and a proximal end having a hub;

an elongate hollow handle with a proximal end and a distal end having an opening therethrough, said proximal end including a female luer fitting for attaching a fluid handling device;

an elongate needle having a sharp distal point, a proximal end and an open passageway therethrough;

an elongate substantially transparent needle hub with a distal end portion having said proximal end of said needle fixedly attached therein, said needle being coaxially slidably disposed within said catheter bore with said catheter hub mounted on said distal end portion of said needle hub and said sharp distal point of said needle projected beyond said tapered distal end of said catheter, said needle hub sized and disposed for coaxial slidable movement within said hollow handle from a first position wherein said needle and said distal end portion of said needle hub project distally outwardly from said handle, said needle hub having a ledge and further including an elongate flashback chamber for receiving and viewing blood flashback therewithin, said flashback chamber fluidly connected to said proximal end of said needle;

said needle hub being operatively biased for an axial movement from said first position to a proximal rest position within said handle wherein said needle with said sharp distal point is substantially contained within said handle, said hollow handle further including a latch member located a proximal distance from said distal end of said hollow handle releasably engaged with said ledge for releasably retaining said needle hub in said first position and a operative trigger to release said latch from said ledge thereby to release said hub for said axial movement to said proximal rest position, said trigger located a proximal distance from said distal end of said hollow handle; and a hollow flexible tube within said hollow handle extending from said proximal end of said hub to said female luer fitting on said proximal end of said hollow handle, said tube fluidly connecting said flashback chamber to said female luer fitting when said hub is in said first position so that a blood sample may be drawn from said flashback chamber, said tube being substantially collapsed when said hub is in said proximal rest position.

* * * * *